US010296723B2

United States Patent
Guo et al.

(10) Patent No.: US 10,296,723 B2
(45) Date of Patent: May 21, 2019

(54) MANAGING COMPANIONSHIP DATA

(71) Applicant: International Business Machines Corporation, Armonk, NY (US)

(72) Inventors: Shang Q. Guo, Cortlandt Manor, NY (US); Canturk Isci, Secaucus, NJ (US); Christopher P. Jones, Las Vegas, NV (US); Jonathan Lenchner, North Salem, NY (US); Daniel A. Mazzella, Henderson, NV (US); Maharaj Mukherjee, Poughkeepsie, NY (US); Rodrigo A. Rey, Las Vegas, NV (US)

(73) Assignee: International Business Machines Corporation, Armonk, NY (US)

( * ) Notice: Subject to any disclaimer, the term of this patent is extended or adjusted under 35 U.S.C. 154(b) by 714 days.

(21) Appl. No.: 14/556,326

(22) Filed: Dec. 1, 2014

(65) Prior Publication Data
US 2016/0154948 A1 Jun. 2, 2016

(51) Int. Cl.
*G06F 19/00* (2018.01)
*G16H 40/63* (2018.01)
(52) U.S. Cl.
CPC .......... *G06F 19/3481* (2013.01); *G06F 19/00* (2013.01); *G16H 40/63* (2018.01)
(58) Field of Classification Search
CPC .. G06F 19/3481; G06F 19/3406; G06F 19/00; G16H 20/30; G16H 20/40; G16H 20/70; G16H 20/90; G16H 40/63
See application file for complete search history.

(56) References Cited

U.S. PATENT DOCUMENTS

| | | | |
|---|---|---|---|
| 9,390,706 B2 * | 7/2016 | Gustafson | G10L 15/265 |
| 2005/0229103 A1 | 10/2005 | King | |
| 2009/0055019 A1 | 2/2009 | Stiehl et al. | |
| 2010/0125182 A1 * | 5/2010 | Schroeter | G06F 19/3418 600/301 |
| 2011/0105979 A1 * | 5/2011 | Schlaeper | A61B 5/0002 604/5.01 |
| 2011/0178803 A1 | 7/2011 | Petrushin | |

(Continued)

FOREIGN PATENT DOCUMENTS

| | | |
|---|---|---|
| CN | 2729807 Y | 9/2005 |
| CN | 103024565 A | 4/2013 |
| WO | 2002075688 A2 | 9/2002 |

OTHER PUBLICATIONS

Lee, C., "Robot nurse escorts and schmooze the elderly", Robot News, Mar. 17, 2006. 4 pages. http://robotnews.wordpress.com/2006/03/17/robot-nurse-escorts-and-schmooze-the-elderly/.

(Continued)

*Primary Examiner* — Victoria P Augustine
*Assistant Examiner* — Gregory D. Moseley
(74) *Attorney, Agent, or Firm* — Jared L. Montanaro

(57) ABSTRACT

Aspects of the disclosure relate to managing companionship data. The managing of companionship data includes establishing a set of companion data. The set of companion data relates to a user. A computer establishes the set of companion data. The computer also collects a set of stimuli. The set of stimuli is associated with the user. Based on the set of stimuli, a portion of the set of companion data is determined. The portion of the set of companion data is provided to the user.

19 Claims, 7 Drawing Sheets

(56) References Cited

U.S. PATENT DOCUMENTS

| | | | | |
|---|---|---|---|---|
| 2011/0283190 | A1* | 11/2011 | Poltorak | G10L 13/033 |
| | | | | 715/716 |
| 2013/0085808 | A1 | 4/2013 | Forbes | |
| 2013/0257877 | A1* | 10/2013 | Davis | A63F 13/12 |
| | | | | 345/473 |
| 2013/0283168 | A1* | 10/2013 | Brown | G06F 3/165 |
| | | | | 715/728 |
| 2015/0198454 | A1* | 7/2015 | Moore | G06F 3/167 |
| | | | | 701/428 |
| 2016/0029962 | A1* | 2/2016 | Hyde | A61B 5/117 |
| | | | | 600/301 |

OTHER PUBLICATIONS

Mell, P., et al., "The NIST Definition of Cloud Computing", Recommendations of the National Institute of Standards and Technology. NIST Special Publication 800-145, Sep. 2011. 7 pages.

Rotolo, C., "Words of Comfort: What to Say When Someone is Dying", AgingCare.com. 3 pages. http://www.agingcare.com/Articles/say-to-someone-who-is-dying-148641.htm © 2014 AgingCare, LLC.

Unknown, "Esther Rantzen launches 'phone friend' service for older people across Manchester", Manchester City Council, Nov. 26, 2012. http://www.manchester.gov.uk/news/article/6490esther_rantzen_launches_phone_friend_service_for_older_people_across_manchester.

Unknown, "New Research Into Robotic Companions for Older People", University of Hertfordshire, Jun. 4, 2013. http://www.herts.ac.uk/news-and-events/latest-news/New-Research-into-Robotic-Companions-for-Older-People.cfm.

\* cited by examiner

MANAGING COMPANIONSHIP DATA

BACKGROUND

The present disclosure relates to computer systems, and more specifically, to managing companionship data.

Some people would benefit from having more interactions with family members and friends. Interacting with family members and friends may have positive health and emotional benefits. For example, a nursing home resident may be happier when they have a phone conversation with a son. For another example, an Alzheimer's patient may have cognitive benefits from being visited regularly by friends.

SUMMARY

Aspects of the disclosure relate to managing companionship data. Aspects of the disclosure include establishing a set of companion data. The set of companion data relates to a user. A computer establishes the set of companion data. The computer also collects a set of stimuli. The set of stimuli is associated with the user. Based on the set of stimuli, a portion of the set of companion data is determined. The portion of the set of companion data is provided to the user.

Aspects of the disclosure may compare the set of stimuli to a set of predetermined user states. The set of predetermined user states may correspond with the set of companion data. The comparison may identify a subset of the set of predetermined user states. The subset of the set of predetermined user states may meet a relevance threshold. The determination of the portion of the set of companion data may include using the comparison. Aspects of the disclosure may establish a set of contentment factors. The set of contentment factors might correspond to both the portion of the set of companion data and the subset of the set of predetermined user states. The determination of the portion of the set of companion data may include using the set of contentment factors. Aspects of the disclosure may detect a user response. The user response may be received from the user in response to providing the user with the portion of the set of companion data. Aspects of the disclosure may update the set of contentment factors based on the set of user responses.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1A:
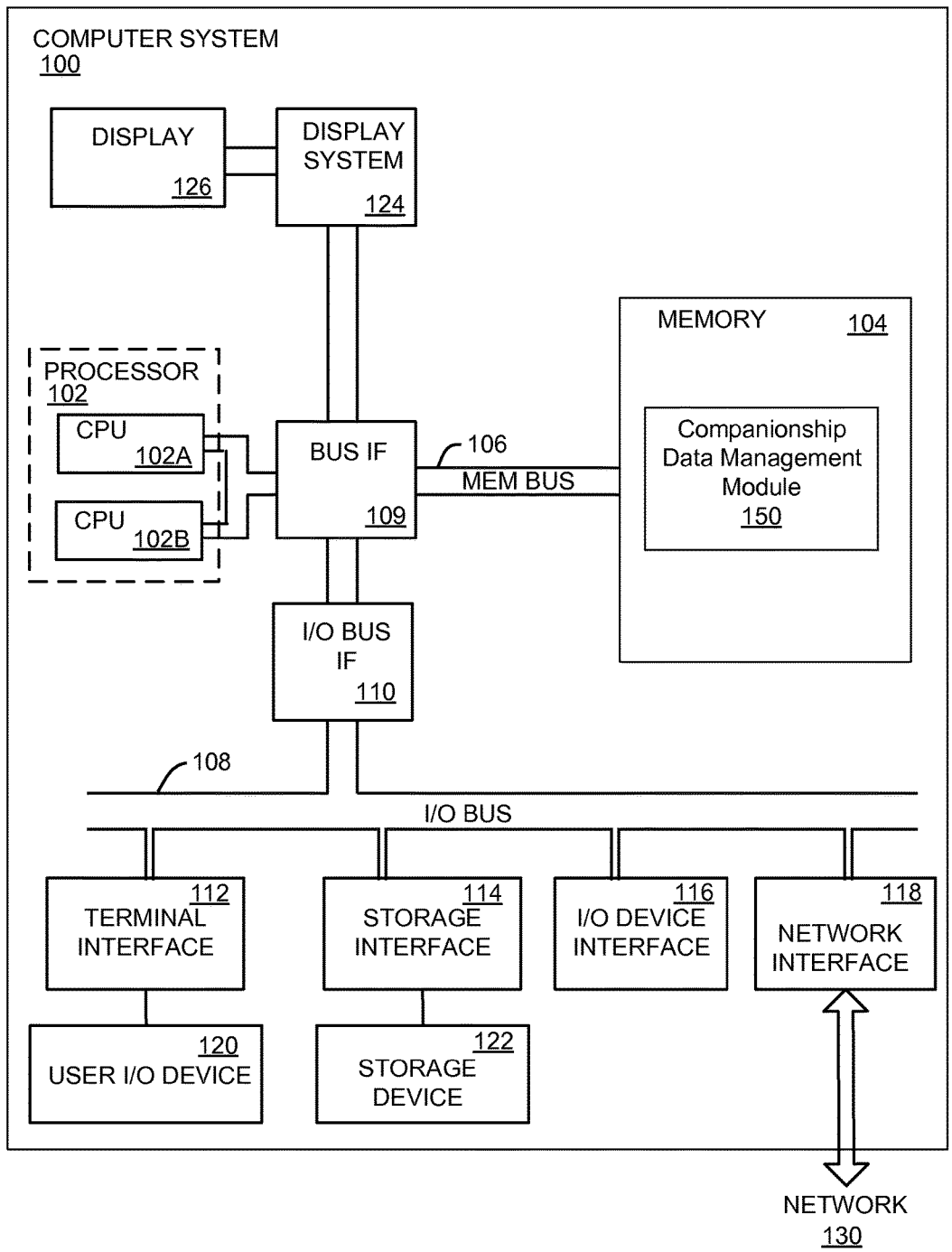
FIG. 1A depicts a high-level block diagram of a system for managing companionship data according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the disclosure include a system and method for managing companionship data to benefit the wellbeing of a user. The user may experience wellbeing benefits via interaction with a simulated companion. Embodiments of the disclosure include observing the user. Particular aspects of the disclosure are directed towards using such observations in order for the simulated companion to respond.

The user may be an individual who would benefit from additional interactions. In some cases the user may not interact with family members and friends as often as desired. To address this, family members or friends can act as a "participant" in the simulated companion interactions. As participants, the family members or friends may receive updates regarding the user. The participants might also provide the simulated companion with new options for interacting with the user. For example, the participants could provide media (e.g., videos of family members) which could be provided to the user. To make the interactions more natural, the user might choose the participant who would be the topic of the interaction, much like choosing a topic of a conversation. When a user chooses a participant, the system and method might provide a response action which relates to the chosen participant. For example, the response action might include media regarding the participant or updates from the participant. Organizing interactions around participants may lead to positive performance/efficiency benefits and improved selection of response actions.

Embodiments of the disclosure are directed toward providing a response action based upon how much the response action is predicted to satisfy the user. Such embodiments can classify the predicted satisfaction of the user with a satisfaction score. Assigning a satisfaction score to different response actions for different situations may lead to performance benefits related to response action selection. To achieve a desired satisfaction score, embodiments of the disclosure are directed toward providing a simulated representation of the participant. The simulated representation may imitate one or more characteristics of the participant. The participant may be imitated with a face generation component or a voice generation component. The face generation component or voice generation component may synthesize a virtual representation of the participant. The face generation component or voice generation component may have access to face images or voice samples of the participant to aid in the synthesis.

A detection component might detect a reaction of the user in response to the response action. The detection component may use emotion detection technology to accurately categorize the reaction of the user. Embodiments of the disclosure are directed toward learning about a relationship between the response action and the satisfaction score from the reaction of the user. Learning about the relationship may improve the determination of the response action. Embodiments of the disclosure are directed toward using machine learning to learn how to respond to a wide variety of inputs. Examples of inputs include a purposeful input such as a question or an indirect input such as a smile. Other inputs are also possible. The breadth of the response capabilities may lead to performance/efficiency benefits and improved satisfaction scores. Accordingly, management of companionship data can include operations for computer-implementation.

Aspects of the disclosure include establishing the set of companion data (e.g., by a computer). The set of companion data (e.g., the response action) relates to the user. In embodiments, the establishing can include the computer receiving new companion data from an external source. In certain embodiments, the establishing can include the participant transmitting the new companion data to the computer. The establishing may also include establishing a set of predetermined user states. The set of predetermined user states may correspond with the set of companion data. The set of predetermined user states categorize input from the user. A set of contentment factors (e.g., satisfaction scores) may be established. The set of contentment factors correspond to both the set of companion data and a subset of the set of predetermined user states.

Aspects of the disclosure include collecting (e.g., by the computer) a set of stimuli. The set of stimuli (e.g., the input) is associated with the user. In embodiments, the set of stimuli includes visual pattern data, motion data, tactile data, temporal data, or auditory data. In certain embodiments, the set of stimuli includes a set of user responses (e.g., the reaction of the user). The computer may transmit the set of stimuli to the participant in response to the set of stimuli meeting a notification threshold.

Aspects of the disclosure include determining a portion of the set of companion data. The portion of the set of companion data is determined based on the set of stimuli. The determined portion can be provided to the user. In an embodiment, determining the portion of the set of companion data can include comparing the set of stimuli to the set of predetermined user states. In such embodiments, a subset of the predetermined user states are identified. The subset of the predetermined user states may be identified by meeting a relevance threshold. In such embodiments, the portion of the set of companion data which is determined may be the portion which corresponds with the subset of the set of predetermined user states. In certain embodiments, determining the portion of the set of companion data can include using the set of contentment factors. The portion of the set of companion data includes visual data, textual data, audio data, or a communication link.

Aspects of the disclosure include providing the portion of the set of companion data to the user. For example, this can include displaying pictures or videos of family members or generating a face or voice of a friend. In embodiments, the set of user responses are detected. Embodiments of the disclosure are directed toward detecting the set of user responses in response to providing the portion of the set of companion data. The set of contentment factors may be updated based on the set of user responses. Organizing companion data around participants or assigning contentment factors to companion data may lead to improved selection of companion data over time.

FIG. 1A depicts a high-level block diagram of a computer system 100 for implementing various embodiments. The mechanisms and apparatus of the various embodiments disclosed herein apply equally to any appropriate computing system. The major components of the computer system 100 include one or more processors 102, a memory 104, a terminal interface 112, a storage interface 114, an I/O (Input/Output) device interface 116, and a network interface 118, all of which are communicatively coupled, directly or indirectly, for inter-component communication via a memory bus 106, an I/O bus 108, bus interface unit 109, and an I/O bus interface unit 110.

The computer system 100 may contain one or more general-purpose programmable central processing units (CPUs) 102A and 102B, herein generically referred to as the processor 102. In embodiments, the computer system 100 may contain multiple processors; however, in certain embodiments, the computer system 100 may alternatively be a single CPU system. Each processor 102 executes instructions stored in the memory 104 and may include one or more levels of on-board cache.

In embodiments, the memory 104 may include a random-access semiconductor memory, storage device, or storage medium (either volatile or non-volatile) for storing or encoding data and programs. In certain embodiments, the memory 104 represents the entire virtual memory of the computer system 100, and may also include the virtual memory of other computer systems coupled to the computer system 100 or connected via a network. The memory 104 can be conceptually viewed as a single monolithic entity, but in other embodiments the memory 104 is a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures.

The memory 104 may store all or a portion of the various programs, modules and data structures for processing data transfers as discussed herein. For instance, the memory 104 can store a companionship data management module 150. In embodiments, the companionship data management module 150 may include instructions or statements that execute on the processor 102 or instructions or statements that are interpreted by instructions or statements that execute on the processor 102 to carry out the functions as further described herein. In certain embodiments, the companionship data management module 150 is implemented in hardware via semiconductor devices, chips, logical gates, circuits, circuit cards, and/or other physical hardware devices in lieu of, or in addition to, a processor-based system. In embodiments, the companionship data management module 150 may include data in addition to instructions or statements.

The computer system 100 may include a bus interface unit 109 to handle communications among the processor 102, the memory 104, a display system 124, and the I/O bus interface unit 110. The I/O bus interface unit 110 may be coupled with the I/O bus 108 for transferring data to and from the various I/O units. The I/O bus interface unit 110 communicates with multiple I/O interface units 112, 114, 116, and 118, which are also known as I/O processors (IOPs) or I/O adapters (IOAs), through the I/O bus 108. The display system 124 may include a display controller, a display memory, or both. The display controller may provide video, audio, or both types of data to a display device 126. The display memory may be a dedicated memory for buffering video data. The display system 124 may be coupled with a display device 126, such as a standalone display screen, computer monitor, television, or a tablet or handheld device display. In one embodiment, the display device 126 may include one or more speakers for rendering audio. Alternatively, one or more speakers for rendering audio may be coupled with an I/O interface unit. In alternate embodiments, one or more of the functions provided by the display system 124 may be on board an integrated circuit that also includes the processor 102. In addition, one or more of the functions provided by the bus interface unit 109 may be on board an integrated circuit that also includes the processor 102.

The I/O interface units support communication with a variety of storage and I/O devices. For example, the terminal interface unit 112 supports the attachment of one or more user I/O devices 120, which may include user output devices (such as a video display device, speaker, and/or television set) and user input devices (such as a keyboard, mouse, keypad, touchpad, trackball, buttons, light pen, or other pointing device). A user may manipulate the user input devices using a user interface, in order to provide input data and commands to the user I/O device 120 and the computer system 100, and may receive output data via the user output devices. For example, a user interface may be presented via the user I/O device 120, such as displayed on a display device, played via a speaker, or printed via a printer.

The storage interface 114 supports the attachment of one or more disk drives or direct access storage devices 122 (which are typically rotating magnetic disk drive storage devices, although they could alternatively be other storage devices, including arrays of disk drives configured to appear as a single large storage device to a host computer, or solid-state drives, such as flash memory). In some embodiments, the storage device 122 may be implemented via any type of secondary storage device. The contents of the memory 104, or any portion thereof, may be stored to and retrieved from the storage device 122 as needed. The I/O device interface 116 provides an interface to any of various other I/O devices or devices of other types, such as printers or fax machines. The network interface 118 provides one or more communication paths from the computer system 100 to other digital devices and computer systems; these communication paths may include, e.g., one or more networks 130.

Although the computer system 100 shown in FIG. 1A illustrates a particular bus structure providing a direct communication path among the processors 102, the memory 104, the bus interface 109, the display system 124, and the I/O bus interface unit 110, in alternative embodiments the computer system 100 may include different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface unit 110 and the I/O bus 108 are shown as single respective units, the computer system 100 may, in fact, contain multiple I/O bus interface units 110 and/or multiple I/O buses 108. While multiple I/O interface units are shown, which separate the I/O bus 108 from various communications paths running to the various I/O devices, in other embodiments, some or all of the I/O devices are connected directly to one or more system I/O buses.

In various embodiments, the computer system 100 is a multi-user mainframe computer system, a single-user system, or a server computer or similar device that has little or no direct user interface, but receives requests from other computer systems (clients). In other embodiments, the computer system 100 may be implemented as a desktop computer, portable computer, laptop or notebook computer, tablet computer, pocket computer, telephone, smart phone, or any other suitable type of electronic device.

FIG. 1A depicts several major components of the computer system 100. Individual components, however, may have greater complexity than represented in FIG. 1A, components other than or in addition to those shown in FIG. 1A may be present, and the number, type, and configuration of such components may vary. Several particular examples of additional complexity or additional variations are disclosed herein; these are by way of example only and are not necessarily the only such variations. The various program components illustrated in FIG. 1A may be implemented, in various embodiments, in a number of different manners, including using various computer applications, routines, components, programs, objects, modules, data structures, etc., which may be referred to herein as "software," "computer programs," or simply "programs."

In addition to embodiments described above, other embodiments having fewer operational steps, more operational steps, or different operational steps are contemplated. Also, some embodiments may perform some or all of the above operational steps in a different order. The modules are listed and described illustratively according to an embodiment and are not meant to indicate necessity of a particular module or exclusivity of other potential modules (or functions/purposes as applied to a specific module).

In the foregoing, reference is made to various embodiments. It should be understood, however, that this disclosure is not limited to the specifically described embodiments. Instead, any combination of the described features and elements, whether related to different embodiments or not, is contemplated to implement and practice this disclosure. Many modifications and variations may be apparent to those of ordinary skill in the art without departing from the scope and spirit of the described embodiments. Furthermore, although embodiments of this disclosure may achieve advantages over other possible solutions or over the prior art, whether or not a particular advantage is achieved by a given embodiment is not limiting of this disclosure. Thus, the described aspects, features, embodiments, and advantages are merely illustrative and are not considered elements or limitations of the appended claims except where explicitly recited in a claim(s).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1B:
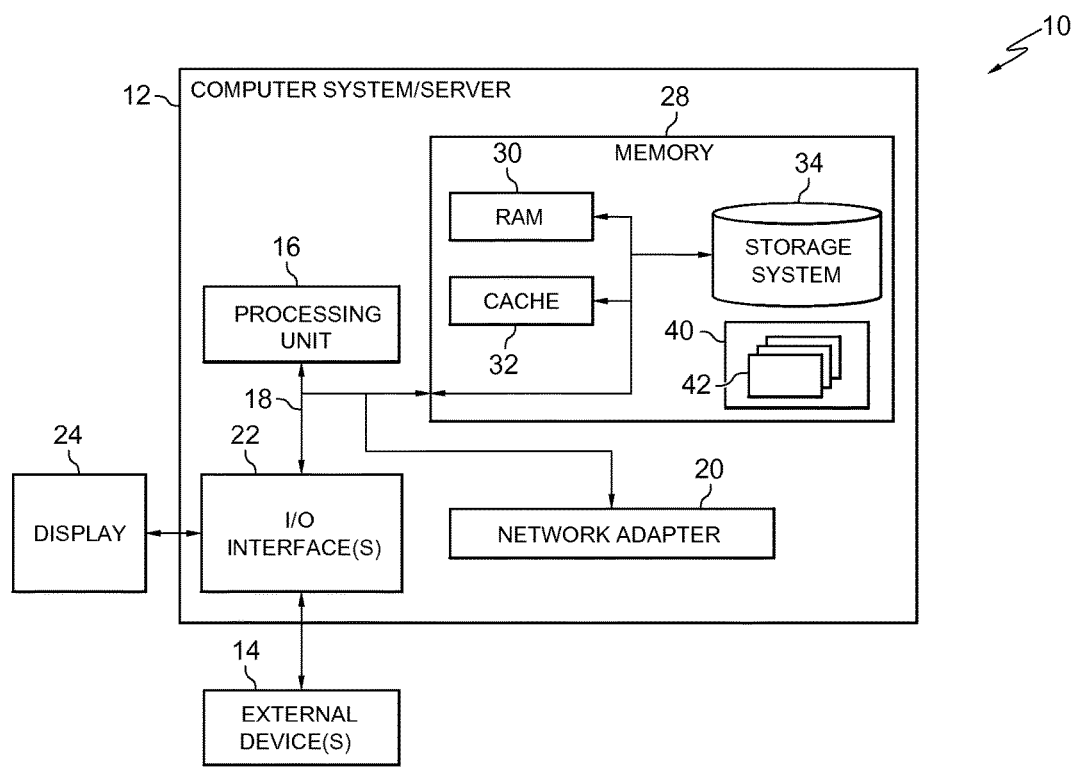
FIG. 1B depicts a cloud computing node according to an embodiment of the present invention.

Referring now to FIG. 1B, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1B, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 1C:
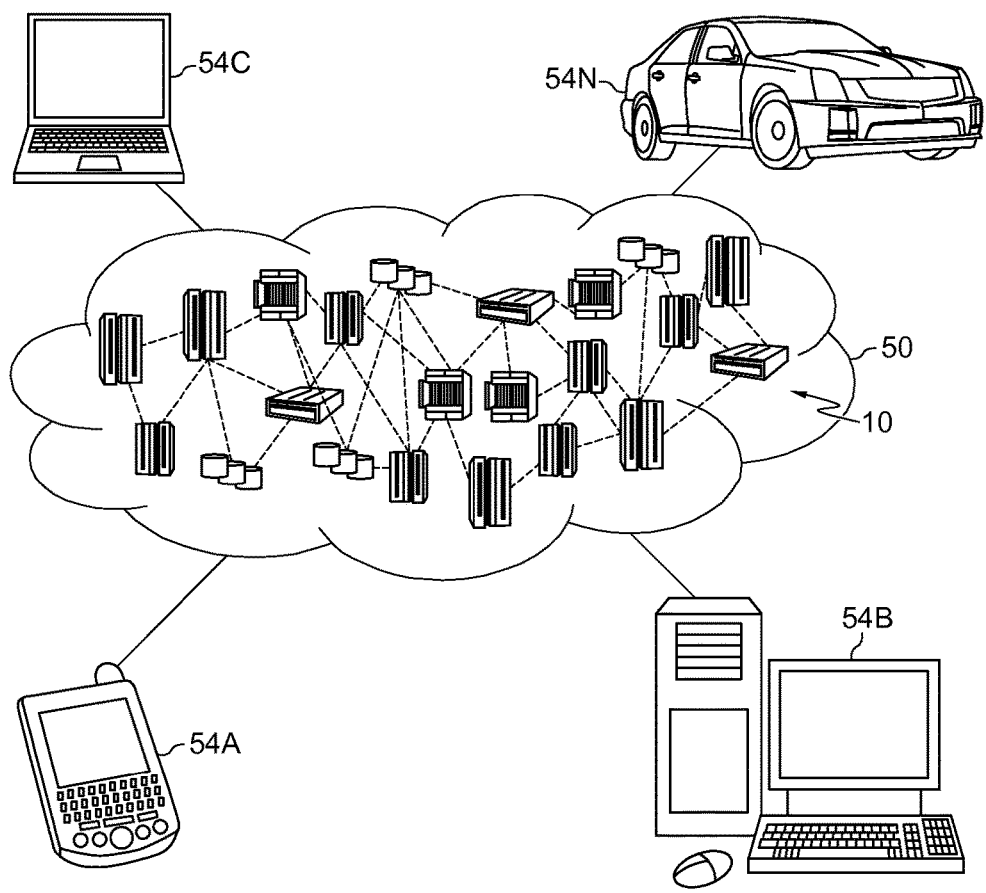
FIG. 1C depicts a cloud computing environment according to an embodiment of the present invention.

Referring now to FIG. 1C, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1C are intended to be illustrative only and that computing nodes 10 and cloud computing environment 50 can communicate with any type of computerized device over any type of network and/or network addressable connection (e.g., using a web browser).

Figure 1D:
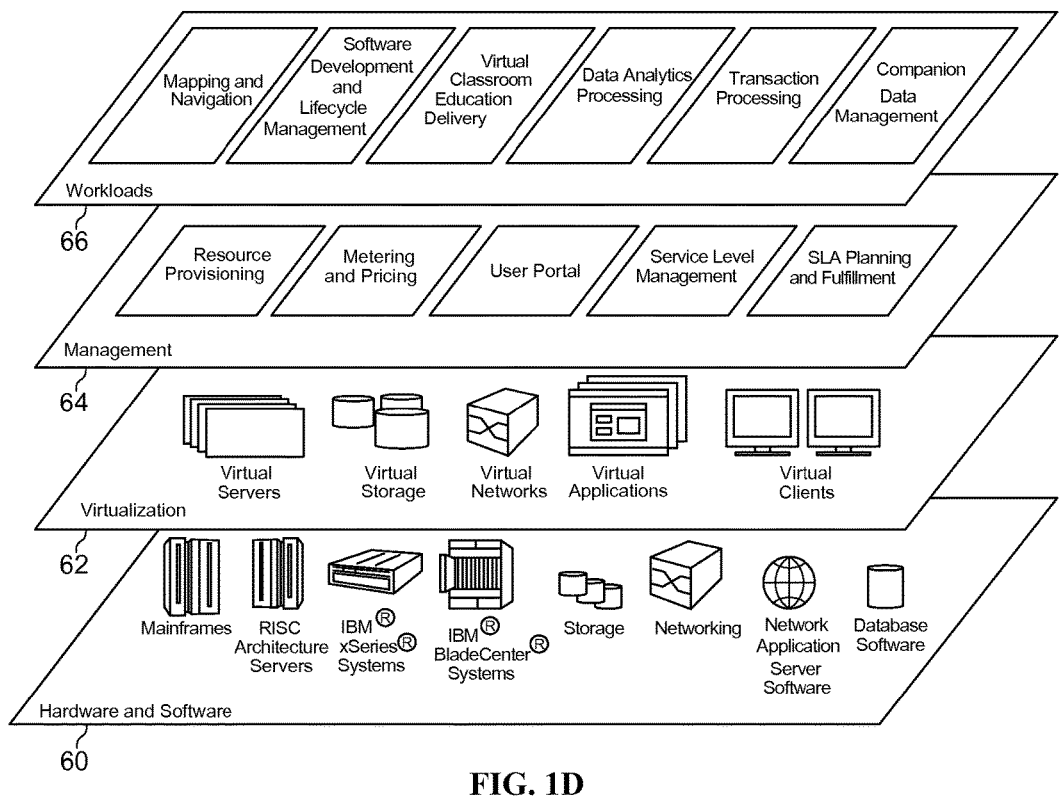
FIG. 1D depicts abstraction model layers according to an embodiment of the present invention.

Referring now to FIG. 1D, a set of functional abstraction layers provided by cloud computing environment 50 (FIG. 1C) is shown. It should be understood in advance that the components, layers, and functions shown in FIG. 1D are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, Series, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and companion data management. Companion data could be managed to simulate interactions with a user. Companion data may be accessed through the cloud computing environment. External sources of companion data may be available through the cloud computer environment. In embodiments, participants may upload companion data through the cloud computing environment.

Figure 2:
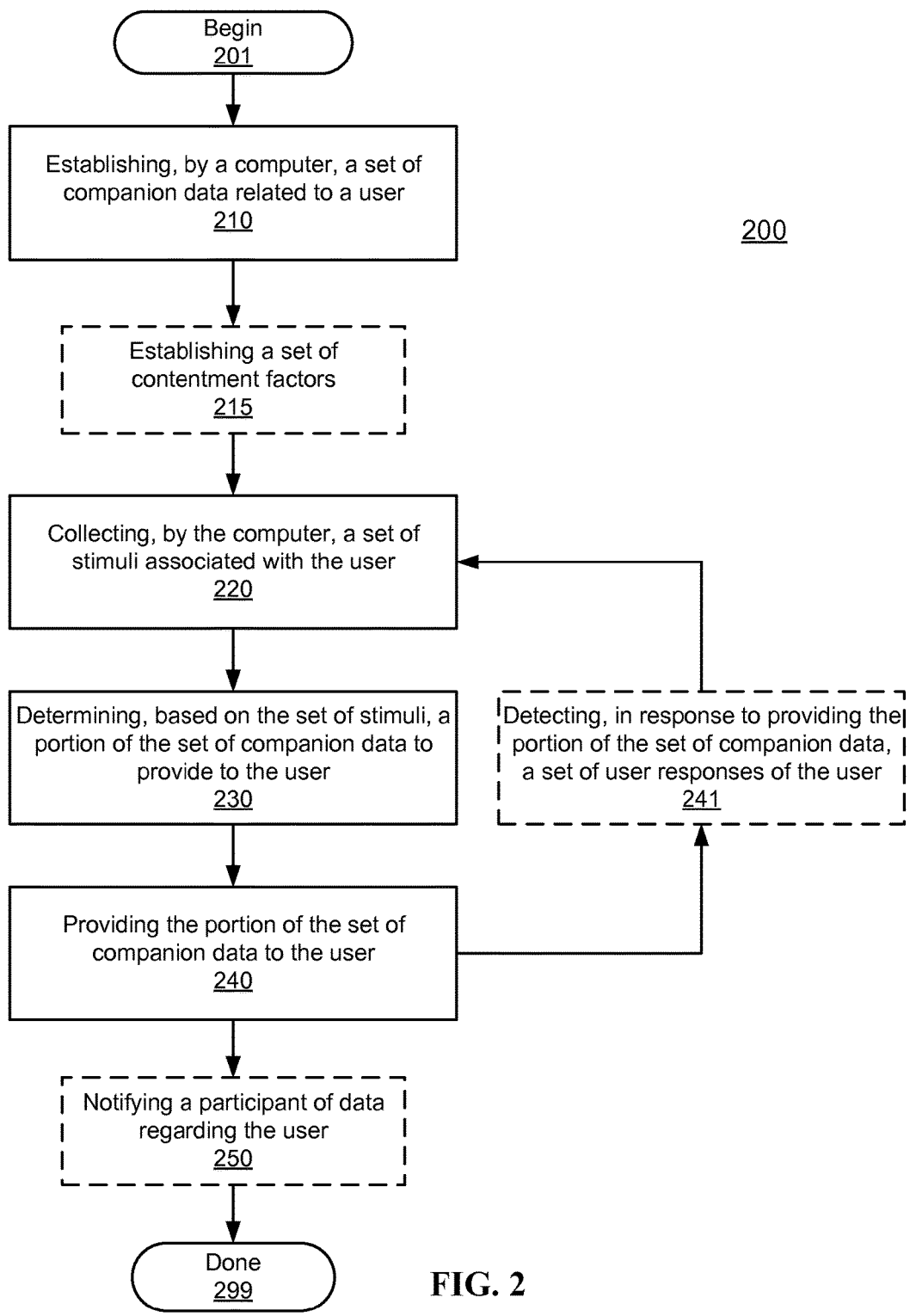
FIG. 2 depicts a method of managing companionship data according to an embodiment.

FIG. 2 is a flowchart illustrating a method 200 for managing companionship data. Aspects of method 200 may work on a number of operating systems. The method 200 begins at block 201. The companionship data is managed for a user. In embodiments the user is a person who might benefit from additional interactions with a companion. For example, the user may be a person meeting an age threshold (e.g., a person over 80 years old), a person meeting a mental threshold (e.g., an Alzheimer's patient), a resident of a nursing home, or the like.

At block 210 a set of companion data is established. The set of companion data is related to the user. The set of data can be established by a computer. In embodiments, the set of companion data can include a set of responses to provide to the user based on the action, behavior, or requests of the user. The set of responses may be provided during a simulated interaction with the user. The set of companion data might include textual data. In embodiments, textual data includes educational reading materials, interesting reading materials, messages from another participant (e.g., a friend or family member of the user), or temporal notifications (e.g., a reminder that today is the birthday of the participant or that a dinner reservation at 15:30 is in 15 minutes). The set of companion data may include visual data. In embodiments, visual data includes educational video clips, a generated face, or pictures or videos related to the participant (e.g., pictures or a video of a grandson playing on a beach). In such embodiments, the generated face imitates the appearance and expressions of the participant. The set of companion data may include audio data, such as a generated voice. In embodiments, the generated voice imitates the voice of the participant saying a statement (e.g., "I had a good day today" or "Are you okay?"). The set of companion data may include a communication link, such as an option to email or call the participant.

The set of companion data is established in one or more ways. In embodiments, the computer may receive new companion data from an external source. In such embodiments, the external source includes a social media application, a network subscription service, or a network media repository. For example, aspects of method 200 can access a social media application/social network which multiple participants (e.g., several siblings and other family members) are connected to. Aspects of method 200 may download an album of wedding pictures or a status update of "I finally graduated from college!" related to one of the participants from the social network. In this example, aspects of method 200 can use natural language processing (NLP) to discern that the participant graduated from college or that wedding pictures of the participant are available for viewing and inform the user accordingly. In embodiments, aspects of method 200 receive a transmission from the participant with new companion data. For example, the participant may upload companion data related to the recent activity of the participant (e.g., a humorous situation which the participant encountered or a big life event the participant is anticipating).

In embodiments, the set of companion data relates to a participant. For example, a first subset of the set of companion data can relate to a participant (e.g., a son of the user). The first subset may contain pictures or updates related to the son. In such embodiments, the set of companion data can also relate to another participant. For example, a second subset of the set of companion data can relate to another participant (e.g., a daughter of the user). The second subset may contain videos or stories related to the family of the daughter. Accordingly, in embodiments the set of companion data might be organized around a set of participants (e.g., the son and daughter).

In embodiments, at block 215 a set of contentment factors are established. In such embodiments, the set of contentment factors can include a quantitative assessment (e.g., numbers, stars, ratings, A+ style grades, etc.) of how the companion data is expected to impact the sentiment of the user. For example, a contentment factor can provide a "score" for how satisfied a user is expected to be after receiving a specific portion of companion data in a specific situation. In certain embodiments, the quantitative assessment may be numbers from 0-100, where a higher score is indicative of more satisfaction. Other embodiments of contentment factors are also possible. In embodiments, each contentment factor corresponds with a pairing of a portion of companion data and a subset of predetermined user states. For example, the set of predetermined user states may include user states such as "smile," "question about son's status," "question about daughter's family," or "crying." Put differently, the set of contentment factors can provide connections between individual user states and companion data portions while scoring said connections in regards to the user's sentiment. For example, the contentment factor corresponding with the pairing of the user state "question of daughter's family" and companion data "videos of daughter's family" may be 85. To further the example, the contentment factor corresponding with the pairing of the user state "question of daughter's family" and companion data of generated voice "are you okay?" may be 15. In other words, videos of the daughter's family are more likely to satisfy the user than a concerned question in this situation.

At block 220, a set of stimuli is collected. The set of stimuli is associated with the user. The set of stimuli can be collected by the computer. In embodiments, the set of stimuli includes data from the environment of the user. In certain embodiments, the data from the environment of the user could include visual pattern data, motion data, tactile data, temporal data, or auditory data. Visual pattern data can include images or characteristics of a face of the user. For example, the method 200 may collect images of the user where the corner of the mouth of the user are relatively raised and the front teeth of the user are now visible (i.e., user is smiling). Motion data can include data points of the position of certain objects in space. For example, the method 200 may collect a set of data points relating to the arm of the user waving or a pet dog with lowered down, pinned-back ears, and tail between its legs. Tactile data can include a key stroke, mouse click, or button pressed by the user (e.g., physical computer system manipulation). Temporal data can include the relative time of the user, such as the fact that it is 15:15 in the time zone of the user and therefore 15 minutes from a supper appointment. Auditory data can include a sound coming from the user, such as laughing, crying, or a statement (e.g., "How is my son John doing today?").

At block 230 a portion of the set of companion data is determined. The portion of the set of stimuli is determined so that it may be provided to the user. The determination is based on the set of stimuli. In embodiments, the determination uses the aforementioned set of predetermined user states. In such embodiments, the set of stimuli can be compared to the set of predetermined user states. A user state may have a number of identifying features (e.g., user state "smile" might have raised corners of mouth, exposed front teeth, or squinting eyes as identifying features). The comparison may try to match the features of the user state to features of the set of stimuli. As more features of the stimuli match the features of a user state with more certainty, the method 200 is more likely to determine that the user state is relevant. A user state might be identified as relevant if it meets a relevance threshold.

For example, the method 200 may use NLP to compare an example stimuli of "how is my son John doing today?" to predetermined user states. The method 200 might identify three features of the stimuli: a lilt to the end of the statement to signify a question, a subject of "son John," and the use of "how" to identify the general nature of the query as regarding status. In such embodiments, the method might identify that the user state "question about son's status" has features of "question," "son John," and "status." Despite the fact that the "how" portion of the stimuli can bring down certainty due to the non-specific nature of the word, the set of stimuli may be 90% relevant to the user state of "question about son's status." This may meet a relevance threshold of 85%. The method 200 might identify "question about son's status" as the subset of predetermined user states which meets the relevance threshold. In such embodiments, the method 200 can then select the portion of the set of companion data which corresponds with the identified subset of predetermined user status. Accordingly, the method 200 can select the generated voice of the son participant saying "I had a good day today" as the corresponding companion data. In this way the method 200 can perform a linear projection matching stimuli with pre-ordained portions of companion data based upon how well the stimuli matches up with predetermined user states.

The determination of the portion of the set of companion data can also use a set of contentment factors. The method 200 may determine the portion of the set of companion data which corresponds with both the present stimuli and a contentment factor which meets the contentment threshold. Contentment factors may correlate to the predicted satisfaction of the user in response to being provided a portion of companion data. In embodiments as described herein, the actual satisfaction of the user can be ascertained through analyzing how the user reactions to the companion data which was provided. In such embodiments, the method 200 can use machine learning to learn how to improve determination of companion data by comparing the actual satisfaction to the predicted satisfaction. In this way the method 200 may dynamically match stimuli with companion data based upon how the companion data is projected to impact the user's sentiment at that moment in time.

For example, in an embodiment the contentment threshold is 80 and the stimuli is matched with the user state "question regarding daughter's family." In such embodiments, the method 200 can analyze the contentment factors of multiple different portions of companion data which correspond with the user state "question regarding daughter's family." The method 200 can determine that "videos of daughter's family" has a contentment factor of 85 which meets the contentment threshold of 80. The method 200 can therefore select "videos of daughter's family" as the companion data to provide to the user.

In embodiments, there might not be a portion of companion data which meets the relevance threshold. For example, the stimuli can be a garbled or oddly worded statement which could not be matched to a user state with a degree of certainty high enough to meet the relevance threshold. In such embodiments, the method 200 can query the user with the predetermined user states which came closest to meeting the threshold (e.g., the method may ask the user, "did you mean 'how is my son doing' or 'how is my daughter doing?'"). In certain embodiments, if the user chooses a proposed user state, the method 200 can add a correlation between the chosen user state and the stimuli. For example, once a user chooses "Jim's status" as the user state for stimuli "How is my youngest doing?" the method 200 can learn the correlation between "my youngest" and "Jim."

Once a user state is selected, the method 200 may process the user state to determine the portion of the set of companion data.

In embodiments, a portion of companion data might not meet the relevance threshold because the stimuli either had no corresponding predetermined user state or no corresponding companion data. For example, a stimuli of "what is the date of my granddaughter's marriage?" may not yet have a corresponding user state of "granddaughter marriage question" or corresponding companion data of "May 30." The method 200 might still query the user with the user states closest to meeting the threshold, in response to which the user may select a null value (e.g., "none of these user states match my question"). In response to the null value, the method 200 might transmit the stimuli to the participant. The method 200 may receive new companion data from the participant as described in block 210 to correspond with the stimuli. The new companion data can then be determined.

At block 240, the portion of the set of companion data is provided to the user. In embodiments, providing the portion of the set of companion data may include presenting to the user the pictures, videos, answers, or materials the method 200 determined in block 230. In providing companion data, the method 200 may generate the face or voice of a participant. For example, a user can use aspects of the method 200 to select a participant John, and then ask, "How is my son John doing today?" In response to the stimuli of this question, the method 200 can imitate the face of John or the voice of John while providing the companion data "I had a good day today." Similarly, the user may select to receive companion data regarding a different participant and the method 200 may pull the subset of companion data associated with that participant as described herein.

In embodiments, at block 241 a user response from the user is detected. The user response can be in response to the method 200 providing the companion data. The method 200 may use the user response to update the set of contentment factors. For example, if the edges of the mouth of the user flatten or turn down and the user's brow furrows, the method 200 might identify the user response as user state "frown." This may mean that the provided companion data did not satisfy the user. Using this information, the method 200 might lower the contentment factor associated with the provided companion data and initial user state commensurate with the user response.

In embodiments, the user response can become a set of stimuli as described herein. For example, in response to providing the user with a video of a grandson, a user may start to frown or cry. The method might receive this new stimuli, categorize it correctly with the user state of "frown" or "cry," and both determine and provide a companion data response of "are you okay?" In this way an incoming set of stimuli can be detected in response to provided companion data, in response to which companion data can be provided, for which a response stimuli can be detected, etc.

In embodiments, at block 250 a participant (e.g., a son or daughter of the user) is notified of data regarding the user. In certain embodiments, the method 200 might send the notification data to a device of the participant over a network. In such embodiments, the method 200 can make use of the "internet of things" to send the data straight to such network-enabled devices as a cell phone, car, laptop, television, watch, or other device owned by the participant. In certain embodiments, the notification can be data related to the set of stimuli. In such embodiments, the method 200 can transmit the set of stimuli to the participant. The set of stimuli may be transmitted to the participant if it meets a notification threshold. In certain embodiments, a notification threshold includes a decibel level. If a set of stimuli from the user meets the decibel level (e.g., if the user is yelling), the participant might receive the set of stimuli. In certain embodiments, a notification threshold includes a visual image factor. The visual image factor may analyze what the user might visually look like in a moment in time and compare this image with threshold images. For example, if a set of stimuli from the user includes a visual image which is categorized into the threshold image "crying," the participant might receive the set of stimuli notifying them that the user is crying. In certain embodiments, a notification can include a pet motion factor. If a set of stimuli from the environment included motion data of a dog with head down, ears back, and tail between its legs which is categorized into "anxious dog," the participant might receive the set of stimuli notifying them of the anxious dog. Other factors within the notification threshold are also possible.

In certain embodiments, a participant may be notified of data related to contentment factor updates. For example, the method 200 can send the participant a notification if the user starts getting better contentment factors from pictures from a few decades ago (e.g., the user is feeling nostalgic) or worse contentment factors from updates regarding a recent news story (e.g., the user does not like hearing about an ongoing natural disaster). By notifying the participant, the method 200 might be more likely to receive and provide companion data which reflects the current desires of the user. This may allow the method 200 to achieve contentment factors which meet the contentment threshold more consistently. Method 200 ends at block 299.

Method 200 may operate in multiple ways. One way the method 200 operates is provided in the following example of an embodiment. The method 200 receives new companion data from a participant. The participant is the user's daughter, Sally. The new companion data from Sally comes with an identification of "vacation pictures." The method 200 categorizes the new companion data as visual data and assign a contentment factor to various portions of companion data. For example, the method 200 assigns a contentment factor of 90 corresponding to user state "asking for vacation pictures," a contentment factor of 85 corresponding to "asking for pictures," a contentment factor of 20 corresponding to user state "question about son's status," and a contentment factor of 86 corresponding to user state "greeting daughter." The method 200 determines these contentment factors values by extrapolating from similar companion data which was previously provided to the user.

After completing all of these operations, the method 200 collects a set of motion points which it identifies as the user waving at a motion sensor. The method 200 also collects audio data of "Good morning, my silly sweet Sally!" The method 200 compares this input to the set of predetermined user states. In certain embodiments, the method identifies a single user state with a relevance over 50%. The single user state is "greeting daughter," with a relevance of 75%. The 75% relevance is below a relevance threshold of 85%. The method 200 asks the user, "Did you mean 'Good morning Sally?'" The users answer in the affirmative. The method 200 adds "silly sweet Sally" as an effective synonym to "Sally."

Using the user state of "greeting daughter," the method 200 searches the set of companion data for a portion which meets the contentment threshold of 80. The method 200 identifies both audio data of participant Sally describing her day with a contentment factor of 81 and "vacation pictures" with a contentment factor of 86. In embodiments, the method 200 selects "vacation pictures," as "vacation pictures" meets the contentment threshold by a larger margin. The method 200 generates a smiling face which imitates participant Sally using stored images of Sally. The method 200 also generates a voice imitating participant Sally saying "Morning! Would you like to see new vacation pictures?" The user answers in the affirmative.

In response to providing the companion data of "vacation pictures, the method 200 detects audio data of the user laughing, audio data of the user saying "these pictures are great," and visual pattern data of the user smiling. The method 200 changes the contentment factor from an 86 to a 96, sending a notification to participant Sally detailing the change. Participant Sally receives the notification through her network-connected watch while walking out the door of her house, and she turns around to upload additional pictures before leaving. The method 200 receives the additional pictures from participant Sally. The method 200 maps the detected audio or visual pattern data of the user to the user state "enjoying family pictures." The method 200 then determines a next portion of companion data to provide for this user state, such as "Would you like to see another batch of new vacation pictures?" In this way the method 200 continues to respond to the user, learning how to select better companion data from the interactions over time. Through the machine learning, the organization of responses around participants, and the scoring of potentially actions based upon predicted responses, the method 200 sees performance benefits in determining companion data.

Figure 3:
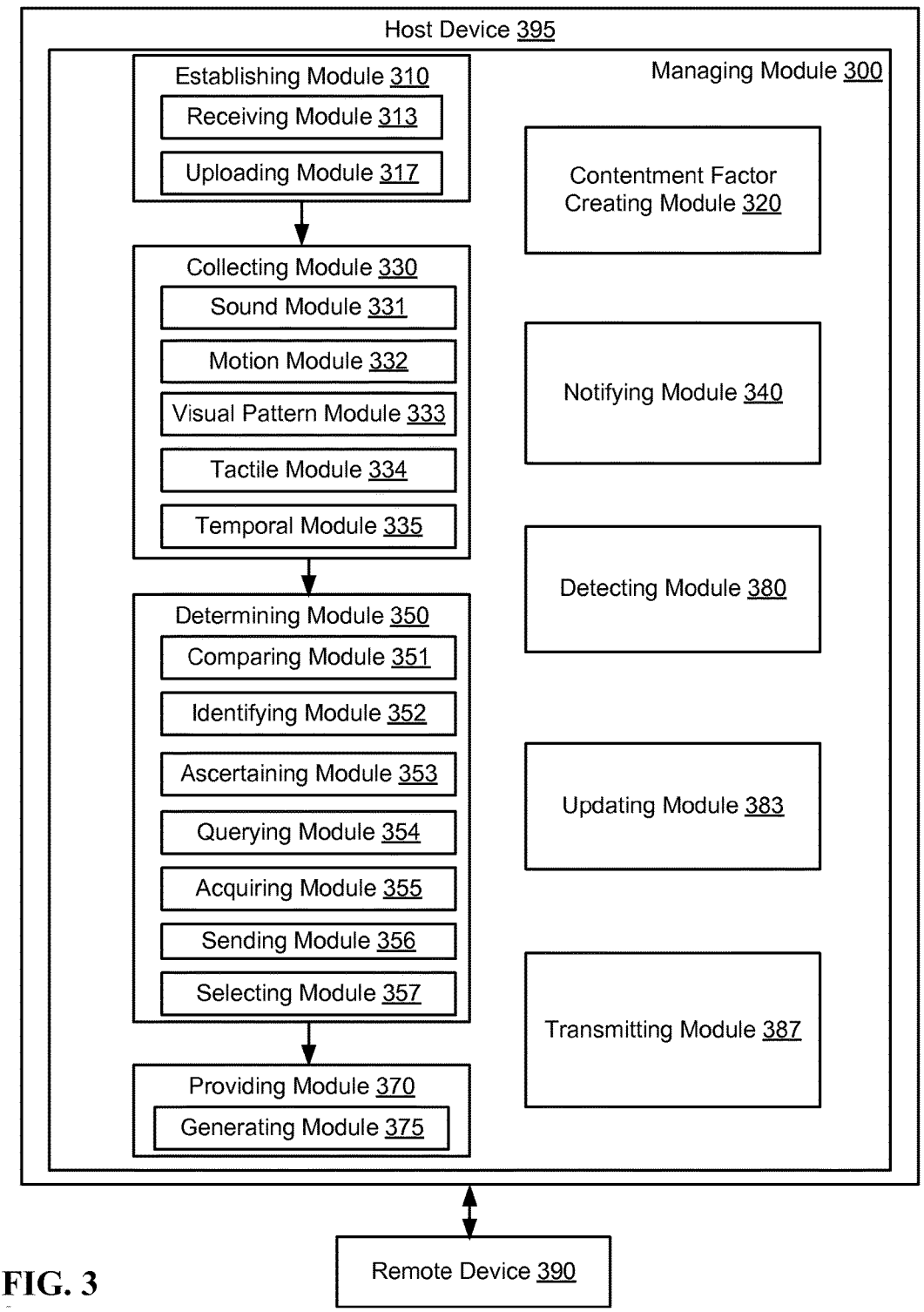
FIG. 3 depicts a system for managing companionship data according to an embodiment.

FIG. 3 shows embodiments of a system for managing companionship data. In embodiments, method 200 can be implemented using one or more modules of FIG. 3. These modules may be implemented in hardware, software, or firmware executable on hardware, or a combination thereof. For example, module functionality that may occur work on a host device 395 may actually be implemented in a remote device 390 and vice versa. Other functionality may be distributed across the host device 395 and the remote device 390.

The host device 395 may include a managing module 300. The managing module 300 is configured and arranged to manage companionship data. The managing module 300 may include an establishing module 310, a receiving module 313, an uploading module 317, a contentment factor creating module 320, a collecting module 330, a sound module 331, a motion module 332, a visual pattern module 333, a tactile module 334, a temporal module 335, a notifying module 340, a determining module 350, a comparing module 351, an identifying module 352, an ascertaining module 353, a querying module 354, an acquiring module 355, a sending module 356, a selecting module 357, a providing module 370, a generating module 375, a detecting module 380, an updating module 383, and a transmitting module 387.

The establishing module 310 establishes a set of companion data. The companion data includes media provided for the user, such as pictures and videos. The pictures and videos may be related to a family member or friend who acts as a participant of the managing module 300. The companion data might include updates regarding the participant, communication links to the participant, or data (e.g., face images or voice samples) for a module to imitate the participant. In embodiments, the establishing module 310 might establish the companion data such that the companion data is organized around the participants. For example, the establishing module 310 can establish a first cluster of data related to participant "John" in one array, and can establish a second cluster of data related to participant "Sally" in a second array.

The establishing module 310 may include the receiving module 313 and the uploading module 317. The receiving module 313 may receive new companion data from an external source. The receiving module 313 might integrate the new companion data into the companion data database. In embodiments, when the new companion data relates to a specific participant, the receiving module 313 can integrate the new companion data into the existing array of companion data which is designated to the specific participant. The uploading module 317 may receive an upload of new companion data. The new companion data can be uploaded by a participant. The uploading module 317 may integrate the new companion data into the existing companion data. In embodiments, when the new companion data relates to a specific participant, the uploading module 317 can integrate the new companion data into the existing array of companion data which is designated to the specific participant.

The contentment factor creating module 320 creates contentment factors. A contentment factor relates to the sentiment/satisfaction of the user when the user is presented with a portion of companion data in a given situation (e.g., a predetermined user state). For example, if a user is highly satisfied when presented with a specific birthday video on the user's birthday, this option (presenting the birthday video on the user's birthday) might have a "better" contentment factor. The contentment factor creating module 320 may establish contentment factors such that each contentment factor corresponds with both a portion of companion data (e.g., a picture, a story, a birthday video) and a predetermined user state (e.g. happy, sad, day of user's birthday).

The collecting module 330 collects a set of stimuli. The set of stimuli is associated with the user. The set of stimuli can be used by the managing module 300 to determine the state of the user (e.g., happy, sad, desiring to see a picture, desiring to see a video). The collecting module may include a sound module 331, motion module 332, visual pattern module 333, tactile module 334, or temporal module 335. The sound module 331 collects sounds associated with the user (e.g., talking, laughing, crying). The motion module 332 collects motions associated with the environment of the user (e.g., the user waving, a pet dog wagging its tail). The visual pattern module 333 collects visual patterns of the user (e.g., facial expressions, body posture). The tactile module 334 collects tactile data related to the user (e.g., button depressions, switch flips). The temporal module 335 collects temporal data related to the user (e.g., the local time of the user relative to appointments of the user). The collecting module 330 may organize the stimuli data from one or more of the aforementioned modules collecting stimuli data. If the final organized stimuli is outside of a notification threshold (e.g., if the stimuli indicates anger, fear, or depression from the user) the notifying module 340 might notify the participant. The notifying module 340 may notify the participant by sending the participant the set of stimuli.

The determining module 350 determines a portion of the set of companion data to provide to the user. The determining module 350 determines the companion data based on the set of stimuli. For example, if the set of stimuli is the user pressing a button on the user's phone in the morning, the determining module 350 might determine to provide the companion data "good morning, user." The determining module 350 may include the comparing module 351, identifying module 352, ascertaining module 353, querying module 354, acquiring module 355, sending module 356, and selecting module 357.

The comparing module 351 compares the set of stimuli with the set of predetermined user states. The identifying module 352 might identify which predetermined user states meet a relevance threshold to the set of stimuli. For example, the visual pattern module 333 may collect visual pattern points showing upturned lips and exposed teeth of the user, which might be 90% relevant to user state "smiling." If the relevance threshold is 75%, the identifying module 352 might identify the user state of "smiling." The selecting module 357 may select the portion of companion data which corresponds to the identified user state.

The ascertaining module 353 may ascertain that no known user state met the relevance threshold. The querying module 354 may query the user. The query might include user states for the user to select from. In embodiments, the user states in the query might be the user states which were the closest to meeting the relevance threshold. The acquiring module can acquire the user's selection of the user states in the query. The selecting module 357 may select the portion of companion data which corresponds to the selected user state. In embodiments, the selection might be a null value (e.g., "I was none of these user states"). The sending module 356 can send the null value and the set of stimuli to a participant.

The selecting module 357 may use the output from the other modules within the determining module 350 to select the portion of companion data to provide to the user as described herein. In embodiments, the selecting module 357 uses contentment factors to select the portion of companion data. For example, the contentment factors might be a number (e.g., 1-100, with higher scores being "better") associated with a pairing of companion data and user states. The selecting module 357 might select the portion of companion data with a corresponding contentment factor which meets a contentment threshold. For example, suppose the identified user state is "smiling," the contentment threshold is 80, and the contentment factor for companion data "how are you doing?" and user state "smiling" is 85. The contentment factor which corresponds to both user state "smiling" and companion data "how are you doing?" can be classified as meeting the contentment threshold. The selecting module 357 can select the portion of companion data (e.g., "how are you doing?") which corresponds to the contentment factor.

The providing module 370 provides the portion of the set of companion data to the user. The providing module 370 may provide companion data by displaying images, playing sounds, providing communication links, or displaying text. The providing module 370 may include the generating module 375. The generating module 375 can imitate the face and voice of participants. Imitating faces of the participants may include simulating expressions of the participants. The generating module 375 can provide statements in the voice of participant. For example, the generating module 275 may generate a face of the participant smiling while saying "I had a good day today" in the voice of the participant.

The detecting module 380 detects a reaction from the user. The reaction may be to the provided companion data. The reaction detected by the detecting module 380 may be sound, motion, visual patterns, or tactile data. In embodiments, the detecting module can use the modules within the collecting module 330 to detect a reaction. The updating module 383 can update the set of contentment factors based upon the reaction. For example, if the contentment factor for a user state and companion data pairing was 95 and the reaction was identified as "frowning," the updating module 383 may update the contentment factor to 50. In embodiments, the updating module 383 can use the comparing module 351 and identifying module 352 to identify a reaction as a user state. The updated contentment factor may be transmitted to the participant by the transmitting module 387.

Figure 4:
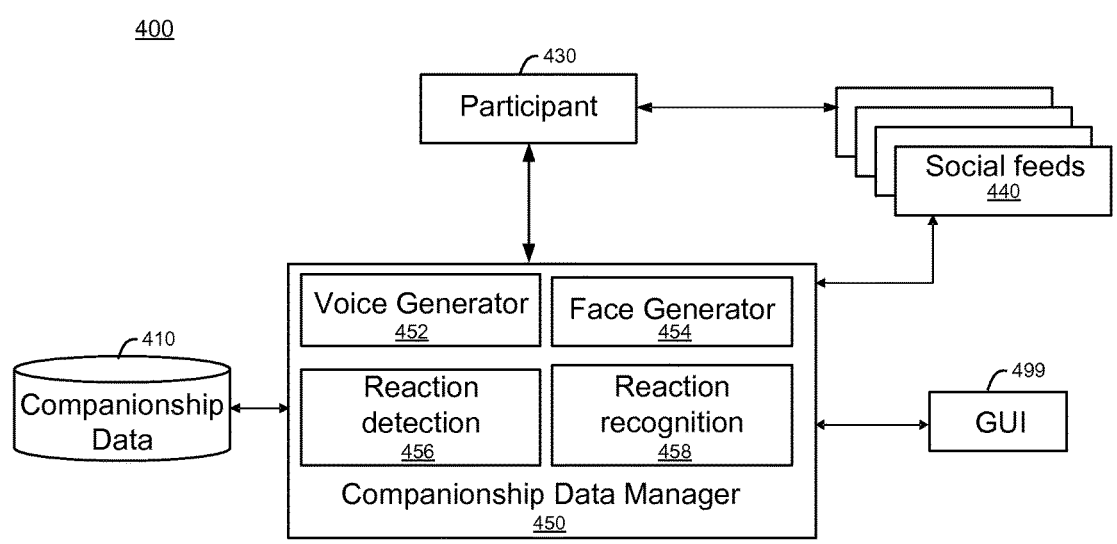
FIG. 4 depicts a system architecture for managing companionship data according to an embodiment.

FIG. 4 shows an embodiment of a system architecture 400. In FIG. 4 the companionship data manager 450 is connected to all components. In certain embodiments, the companionship data manager 450 may be analogous to the managing module 300 from FIG. 3. The companionship data manager 450 may determine what companion data to provide. Many components include a voice generator 452 and a face generator 454 (e.g., the generating module 375) for imitating a participant while providing companion data. The companion data might be stored in an external companionship data database 410. The companion data manager 450 may also contain a reaction detection component 456 which can detect a reaction from the user in response to the provided companion data. The reaction recognition component 458 recognizes the reaction as belonging to a particular user state (e.g., frowning, smiling). For example, the reaction recognition component 458 may use natural language processing (NLP) to process speech or facial recognition technology to process facial expressions.

An external participant 430 may communicate with the companionship data manager 450 as described herein. The companionship data manager 450 may also receive companion data from external social feeds 440 which the participant is linked to. Social feeds might include central network media dumps. Once companion data is determined using these components, the companionship data manager 450 can provide the companion data to the user through an external graphical user interface (GUI) 499.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein. The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method for managing companionship data, comprising:
   acquiring participant data from one or more participants, wherein the participant data includes one or more images of the one or more participants and one or more audio fragments corresponding to voices of the one or more participants;
   receiving a first statement from a user, wherein the first statement includes a mention of a participant, wherein the participant is selected from the one or more participants, wherein the mention of the participant is a correlated designation of the participant, and wherein the mention of the participant indicates which of the one or more participants is to be simulated;
   generating a simulated face of the participant using one or more images of the participant, wherein the one or more images of the participant are selected from the one or more images of the one or more participants;
   generating a simulated voice of the participant using one or more audio fragments corresponding to the voice of the participant, wherein the one or more audio fragments corresponding to the voice of the participant are selected from the one or more audio fragments corresponding to the voices of the one or more participants;
   establishing, by a computer, a set of companion data related to the user, wherein the set of companion data includes a first portion, and wherein the first portion includes data for presenting the simulated face and simulated voice of the participant to the user, the simulated face and simulated voice of the participant constructed, in response to receiving the first statement, to replicate a first facial motion and a first phrase associatively expressed by the participant;
   presenting the simulated face and simulated voice of the participant to the user, the simulated face and simulated voice of the participant replicating the first facial motion and the first phrase;
   collecting, by the computer, a first set of stimuli associated with the user in response to the user being presented with the simulated face and simulated voice of the participant replicating the first facial motion and the first phrase, wherein the first set of stimuli is collected using motion data of the user's face, the motion data being collected by data points associated with one or more positions of the user's face during the presentation of the first facial motion and the first phrase;
   determining, based on the first set of stimuli, a second portion of the set of companion data to provide to the user;
   presenting the simulated face and simulated voice of the participant to the user, the simulated face and simulated voice of the participant constructed to replicate a second facial motion and a second phrase associatively expressed by the participant; and
   providing the second portion to the user.

2. The method of claim 1, wherein determining the second portion to provide to the user, includes:
   comparing the first set of stimuli with a set of predetermined user states which corresponds with the set of companion data;
   identifying a subset of the set of predetermined user states which meets a relevance threshold, wherein identifying the subset of the set of predetermined user states which meets the relevance threshold includes:
      identifying one or more facial expressions of the user,
      ranking the one or more facial expressions of the user, and
      determining a first facial expression is a certain facial expression; and
   selecting the second portion, the second portion corresponding to the subset of the set of predetermined user states.

3. The method of claim 2, further comprising:
   establishing a set of contentment factors corresponding to both the second portion and the subset of the set of predetermined user states; and
   generating, respectively, a numeric value associated with each predetermined user state of the set of predetermined user states, wherein the respective numeric values are related to an indication of user satisfaction.

4. The method of claim 3, wherein determining the second portion to provide to the user includes using the set of contentment factors, further comprising:
  detecting, in response to providing the second portion, a set of user responses of the user; and
  updating the set of contentment factors based on the set of user responses.

5. The method of claim 4, wherein determining the second portion to provide to the user using the set of contentment factors includes:
  identifying a contentment factor of the set of contentment factors which meets a contentment threshold; and
  selecting the second portion, the second portion corresponding to the contentment factor and the subset of the set of predetermined user states.

6. The method of claim 1, wherein establishing the set of companion data related to the user includes an operation selected from a group consisting of at least one of:
  receiving, by the computer from an external source, new companion data; or
  transmitting, from the participant to the computer, the new companion data.

7. The method of claim 6, wherein the external source includes an entity selected from a group consisting of at least one of: social media applications used by a set of the one or more participants, network subscriptions used by a set of the one or more participants, or network media repositories used by a set of the one or more participants.

8. The method of claim 1, further comprising transmitting the first set of stimuli to the participant in response to the first set of stimuli meeting a notification threshold.

9. The method of claim 4, further comprising notifying, in response to updating the set of contentment factors, the participant.

10. The method of claim 1, wherein the user includes an entity selected from a group consisting of at least one of: an individual meeting an age threshold, an individual meeting a cognitive threshold, or an individual in a nursing home.

11. The method of claim 2, wherein determining the second portion to provide to the user includes:
  detecting that the subset of the set of predetermined user states fails to meet the relevance threshold;
  querying, in response to detecting the subset of the set of predetermined user states fails to meet the relevance threshold, the user with the set of predetermined user states;
  receiving, from the user, a selection of the set of predetermined user states; and
  processing the selection of the set of predetermined user states.

12. The method of claim 11, wherein processing the selection of the set of predetermined user states includes transmitting the first set of stimuli to the participant.

13. The method of claim 4, further comprising transmitting a set of data to the participant over a network to a device of the participant, wherein the set of data includes data selected from a group consisting of at least one of:
  the first set of stimuli; and
  the set of contentment factors.

14. A system for managing companionship data, the system comprising:
  a memory; and
  a processor in communication with the memory, the processor being configured to perform operations comprising:
  acquiring participant data from one or more participants, wherein the participant data includes one or more images of the one or more participants and one or more audio fragments corresponding to voices of the one or more participants;
  receiving a first statement from a user, wherein the first statement includes a mention of a participant, wherein the participant is selected from the one or more participants, wherein the mention of the participant is a correlated designation of the participant, and wherein the mention of the participant indicates which of the one or more participants is to be simulated;
  generating a simulated face of the participant using one or more images of the participant, wherein the one or more images of the participant are selected from the one or more images of the one or more participants;
  generating a simulated voice of the participant using one or more audio fragments corresponding to the voice of the participant, wherein the one or more audio fragments corresponding to the voice of the participant are selected from the one or more audio fragments corresponding to the voices of the one or more participants;
  establishing, by a computer, a set of companion data related to the user, wherein the set of companion data includes a first portion, and wherein the first portion includes data for presenting the simulated face and simulated voice of the participant to the user, the simulated face and simulated voice of the participant constructed, in response to receiving the first statement, to replicate a first facial motion and a first phrase associatively expressed by the participant;
  presenting the simulated face and simulated voice of the participant to the user, the simulated face and simulated voice of the participant replicating the first facial motion and the first phrase;
  collecting, by the computer, a first set of stimuli associated with the user in response to the user being presented with the simulated face and simulated voice of the participant replicating the first facial motion and the first phrase, wherein the first set of stimuli is collected using motion data of the user's face, the motion data being collected by data points associated with one or more positions of the user's face during the presentation of the first facial motion and the first phrase;
  determining, based on the first set of stimuli, a second portion of the set of companion data to provide to the user;
  presenting the simulated face and simulated voice of the participant to the user, the simulated face and simulated voice of the participant constructed to replicate a second facial motion and a second phrase associatively expressed by the participant; and
  providing the second portion to the user.

15. A computer program product for managing companionship data, the computer program product disposed upon a computer readable storage medium, the computer program product comprising computer program instructions that, when executed by a computer processor of a computer, cause the computer to carry out the steps of:
  acquire participant data from one or more participants, wherein the participant data includes one or more images of the one or more participants and one or more audio fragments corresponding to voices of the one or more participants;
  receive a first statement from a user, wherein the first statement includes a mention of a participant, wherein the participant is selected from the one or more participants, wherein the mention of the participant is a correlated designation of the participant, and wherein the mention of the participant indicates which of the one or more participants is to be simulated;
generate a simulated face of the participant using one or more images of the participant, wherein the one or more images of the participant are selected from the one or more images of the one or more participants;
generate a simulated voice of the participant using one or more audio fragments corresponding to the voice of the participant, wherein the one or more audio fragments corresponding to the voice of the participant are selected from the one or more audio fragments corresponding to the voices of the one or more participants;
establish, by a computer, a set of companion data related to the user, wherein the set of companion data includes a first portion, and wherein the first portion includes data for presenting the simulated face and simulated voice of the participant to the user, the simulated face and simulated voice of the participant constructed, in response to receiving the first statement, to replicate a first facial motion and a first phrase associatively expressed by the participant;
presenting the simulated face and simulated voice of the participant to the user, the simulated face and simulated voice of the participant replicating the first facial motion and the first phrase;
collect, by the computer, a first set of stimuli associated with the user in response to the user being presented with the simulated face and simulated voice of the participant replicating the first facial motion and the first phrase, wherein the first set of stimuli is collected using motion data of the user's face, the motion data being collected by data points associated with one or more positions of the user's face during the presentation of the first facial motion and the first phrase;
determine, based on the first set of stimuli, a second portion of the set of companion data to provide to the user;
present the simulated face and simulated voice of the participant to the user, the simulated face and simulated voice of the participant constructed to replicate a second facial motion and a second phrase associatively expressed by the participant; and
provide the second portion to the user.

16. The method of claim 1, wherein the correlated designation of the participant includes the computer associating one or more words with the participant.

17. The method of claim 16, wherein the computer associates one or more words with the participant by determining that the user synonymously refers to the participant as the one or more words.

18. The method of claim 17, wherein determining that the user synonymously refers to the participant as the one or more words comprises:
identifying that the user selects a user state from a set of predetermined user states, wherein the user state includes the correlated designation of the participant when the computer collects a stimulus that includes a relative expression.

19. The method of claim 18, further comprising:
receiving, in response to being provided the second portion, a second statement from the user;
presenting a third portion to the user, wherein the third portion includes the simulated face and simulated voice of the participant constructed, in response to receiving the second statement, to replicate a third facial motion and a third phrase associatively expressed by the participant;
collecting, by the computer, a second set of stimuli associated with the user in response to being presented with the simulated face and simulated voice of the participant replicating the third facial motion and the third phrase, wherein the second set of stimuli is collected using motion data of the user's face, the motion data collected by data points associated with one or more positions of the user's face during the presentation of the third facial motion and the third phrase;
determining, based on the second set of stimuli, a fourth portion of the set of companion data to provide to the user;
presenting the simulated face and simulated voice of the participant to the user, the simulated face and simulated voice of the participant constructed to replicate a fourth facial motion and a fourth phrase associatively expressed by the participant; and
providing the fourth portion to the user.

* * * * *